US009963425B2

(12) United States Patent
Jaworska-Maslanka et al.

(10) Patent No.: US 9,963,425 B2
(45) Date of Patent: May 8, 2018

(54) BETAINES WITH SPECIAL FATTY ACID CHAIN DISTRIBUTION

(71) Applicant: Evonik Degussa GmbH, Essen (DE)

(72) Inventors: Maria Jaworska-Maslanka, Concord, OH (US); Uwe Begoihn, Essen (DE); Oliver Springer, Wesel (DE); Dominik Schuch, Haan (DE); Ralf Klein, Velbert (DE)

(73) Assignee: Evonik Degussa GmbH, Essen (DE)

( * ) Notice: Subject to any disclaimer, the term of this patent is extended or adjusted under 35 U.S.C. 154(b) by 0 days. days.

(21) Appl. No.: 15/010,219

(22) Filed: Jan. 29, 2016

(65) Prior Publication Data
US 2016/0221935 A1 Aug. 4, 2016

(30) Foreign Application Priority Data

Jan. 30, 2015 (EP) .................................... 15153151

(51) Int. Cl.
*C07C 271/22* (2006.01)
*B01F 17/00* (2006.01)
*C07C 233/36* (2006.01)
*C11D 1/90* (2006.01)
*A61K 8/44* (2006.01)
*A61K 47/18* (2017.01)
*A61Q 19/00* (2006.01)
*C11D 3/00* (2006.01)

(52) U.S. Cl.
CPC .............. *C07C 271/22* (2013.01); *A61K 8/44* (2013.01); *A61K 47/186* (2013.01); *A61Q 19/00* (2013.01); *B01F 17/0042* (2013.01); *C07C 233/36* (2013.01); *C11D 1/90* (2013.01); *C11D 3/0015* (2013.01); *A61K 2800/48* (2013.01)

(58) Field of Classification Search
CPC ....... C07C 271/22; C07C 233/36; C11D 1/90; B01F 17/0042
See application file for complete search history.

(56) References Cited

U.S. PATENT DOCUMENTS

| 4,497,825 | A | 2/1985 | Bade |
| 5,354,906 | A | 10/1994 | Weitemeyer et al. |
| 7,163,916 | B2* | 1/2007 | Allef .................... C07C 231/12 510/340 |
| 7,297,675 | B2 | 11/2007 | Allef et al. |
| 8,138,372 | B2 | 3/2012 | Herrwerth et al. |
| 8,338,348 | B2* | 12/2012 | Anim-Danso ........... A61K 8/39 424/70.11 |

FOREIGN PATENT DOCUMENTS

| DE | 10 2007 005 942 | 8/2008 |
| EP | 0 656 346 | 6/1995 |

OTHER PUBLICATIONS

Crombie, W.M., Fat metobolism in the West African Oil Palm (*Elaeis guineensis*), 1956, Journal of Experimental Botany, vol. 7, No. 20, pp. 181-193.*
Montoya, C., et al., Quantitative trait loci (QTL's) analysis of palm oil fatty acid composition in an interspecific pseudo-backcross from Elaeis oleifer (H.B.K.) Cortes and oil palm (Elaeis guineenis Jacq.), 2013, Tree Genetics & Genomes, vol. 9, pp. 1207-1225.*
Bereau, D., et al., Fa and unsponifiable compositoin of five Amazonian Palm Kernel Oll, 2003, JAOCS, vol. 80, No. 1, pp. 49-53.*
Tan B. K., et al., Characteristics of Kernel Olls from Elaeis oleifera, F1 Hybrids and BAck-cross with Elaeis guineensis, 1982, Journal Sci. Food Agric., vol. 33, pp. 204-208.*
European Search Report for related European application EP 16151401.3 with machine translation of portions of the search report attached, dated May 24, 2016.
European Search Report for corresponding EP application 15153151.4 dated Jul. 16, 2015.
Kao Chemicals: "BETADET HR 2," (Jan. 2013); XP055201919.
"Product Catalog: Classic Surfactants," (Sep. 2013); XP055201891.
New Natural Ingredients Directory—HAPPI: Happy Household and Personal Products Industry (Jul. 2010); XP055202103.

* cited by examiner

*Primary Examiner* — Yate' K Cutliff
(74) *Attorney, Agent, or Firm* — Law Office of Michael A. Sanzo, LLC

(57) ABSTRACT

A subject-matter of the invention are betaines with a special fatty acid chain distribution, for example based on palm kernel oil, the palm kernel oil comprising an enhanced content of unsaturated $C_{18}$ fatty acids.

20 Claims, No Drawings

BETAINES WITH SPECIAL FATTY ACID CHAIN DISTRIBUTION

CROSS REFERENCE TO RELATED APPLICATIONS

The present application claims priority to European Application, EP 15153151.4, filed on Jan. 30, 2015, the contents of which is incorporated herein by reference in its entirety.

FIELD OF THE INVENTION

A subject-matter of the invention are betaines with a special fatty acid chain distribution, for example based on palm kernel oil, the palm kernel oil comprising an enhanced content of unsaturated $C_{18}$ fatty acids.

STATE OF THE ART

At present, use is predominantly made industrially of betaines based on coconut fat. In particular, highly concentrated betaines with a high active content have hitherto been available virtually exclusively as cocamidopropyl betaines based on coconut fat. Native coconut fat exhibits an oleic acid (C18:1) content of at most 10% by weight, based on all fatty acids present in the triglyceride; the industrial fatty acid fractions used for the preparation of the betaines accordingly exhibit an oleic acid content of between 0 and 10% by weight.

Coconut oil differs from palm kernel oil in its fatty acid chain distribution, in particular in the oleic acid content, which is generally from 5% by weight to 10% by weight for coconut oil and generally from 10% by weight to 20% by weight for palm kernel oil.

EP 1 659 109 discloses a process for the preparation of highly concentrated flowable and pumpable aqueous solutions of betaines with a betaine content of at least 32% by weight by quaternization of compounds comprising tertiary amine nitrogen with ω-halocarboxylic acids with addition of micellar thickeners. Optionally hardened coconut fatty acid or palm kernel fatty acid mixtures are proposed as fatty acids; admittedly, in the examples, processing is carried out only with coconut fat.

EP 0 560 114 discloses aqueous liquid solutions of a betaine based on acyl radicals of preferably hardened coconut fatty acids or a fatty acid mixture corresponding on average to coconut fatty acid, the solution exhibiting a solids content of at least 40% by weight, a pH of 5 to 8 and an aminoamide content of <=1% by weight, characterized by a content of 1 to 3% by weight (based on solution) of one or more saturated fatty acids with on average from 8 to 18 carbon atoms or one or more unsaturated fatty acids with on average from 8 to 24 carbon atoms and 0 to 4% by weight (based on solution) of glycerol. Optionally hardened coconut fatty acid or palm kernel fatty acid mixtures are proposed as fatty acids, hardened fatty acid mixtures being preferred. In the examples, processing is carried out only with coconut fat or fats exhibiting a maximum oleic acid content of 11%.

It was an object of the invention to provide novel betaines which, in contrast to the known betaines, exhibit improved performance properties, such as a good foaming behaviour and/or an improved thickenability.

DESCRIPTION OF THE INVENTION

It has been found, surprisingly, that betaines based on palm kernel fat which are derived from a special palm kernel fat with an enhanced oleic acid content in the fatty acid chain distribution have performance advantages.

TABLE 1

Fatty acid chain distribution (details in percentage by weight) of coconut fat and palm kernel fat based on gas chromatography analyses according to *Codex Alimentarius of the Food and Agriculture Organization of the United Nations* (CODEX STAN 210-1999)

| Fatty acid radical | C8:0 | C10:0 | C12:0 | C14:0 | C16:0 | C18:0 | C18:1 | C18:2 |
|---|---|---|---|---|---|---|---|---|
| Coconut fat | 4.6-10.0 | 5.0-8.0 | 45.1-53.2 | 16.8-21.0 | 7.5-10.2 | 2.0-4.0 | 5.0-10.0 | 1.0-2.5 |
| Palm kernel fat | 2.4-6.4 | 2.6-5.0 | 45.0-55.0 | 14.0-18.0 | 6.5-10.0 | 1.0-3.0 | 12.0-19.0 | 1.0-3.5 |

TABLE 2

Fatty acid chain distribution (details in percentage by weight) of coconut fat and palm kernel fat based on gas chromatography analyses according to Thieme RÖMPP Online, Georg Thieme Verlag, 2014

| Fatty acid radical | C8:0 | C10:0 | C12:0 | C14:0 | C16:0 | C18:0 | C18:1 | C18:2 |
|---|---|---|---|---|---|---|---|---|
| Coconut fat | 5-10 | 5-8 | 45-53 | 17-21 | 7-10 | 2-4 | 5-10 | <2 |
| Palm kernel fat | 3 | 5 | 47-52 | 16 | 6-9 | 2-3 | 10-18 | 1-3 |

Commercially available betaines were accordingly already disclosed in the 1980s in DE2926479, which describes a process for the preparation of betaines based on fatty acids with from 6 to 18 carbon atoms by quaternization of fatty acid amides with w-haloalkylcarboxylic acids in aqueous solution. In the examples, processing is carried out with coconut fat.

The present invention therefore relates to fatty acid amidoalkyl betaines. The invention further relates to the use of the fatty acid amidoalkyl betaines in cosmetic, pharmaceutical and industrial applications.

An advantage of the present invention is the improved thickenability of, particularly, aqueous surfactant formulations. Accordingly, higher viscosities in aqueous surfactant formulations with analogous composition can be achieved in the presence of the betaines of the invention compared to betaines not of the invention. Furthermore, on replacing the betaines not of the invention with betaines according to the invention, the amount of added thickener or sodium chloride in the formulation can be reduced without loss in viscosity. Alternatively, with a thickener concentration which remains the same, the amount of the betaine according to the invention can also be reduced without loss in viscosity. Accordingly, the betaines according to the invention generally make possible a reduction in the total concentration of a cosmetic surfactant formulation, resulting in a greater efficiency. In addition, reduced salt contents advantageously have an effect on the mildness, the skin feel and the corrosiveness of surfactant formulations.

An additional advantage of the betaines of the invention is a strengthened and faster foam development with stirring, shaking or any other shear force action in aqueous solution in comparison with betaines not according to the invention. A strengthened foam formation is accomplished by the user typically with a reduction in the amount used and accordingly a saving in resources.

A further advantage of the betaines according to the invention is a reduction in the stiffness after application to woven fabric, in comparison with betaines not according to the invention.

A further advantage of the betaines according to the invention is an increase in the softness after application to woven fabric, in comparison with betaines not according to the invention.

The present invention accordingly relates to fatty acid amidoalkyl betaines of the general formula I:

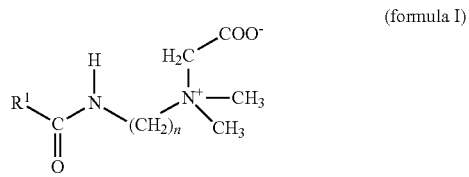

(formula I)

with n=1 to 10, preferably 2 to 5, in particular 3, and $R^1CO$=mixture of acyl radicals of a palm kernel oil, characterized in that the mixture of the acyl radicals exhibits an oleic acid acyl radicals content, based on all acyl radicals of the mixture, of 12% by weight to 21% by weight, preferably of 13% by weight to 17% by weight and particularly preferably of 14% by weight to 15% by weight.

Accordingly, in the present case, a mixture of fatty acid amidoalkyl betaines is claimed.

The term "mixture of acyl radicals of a palm kernel oil" is understood to mean, in connection with the present invention, that this mixture comprises the following listed amount of each acyl radical, given as percentage by weight, the percentages by weight mentioned being with reference to all acyl radicals present in the mixture:

| C8:0 | C10:0 | C12:0 | C14:0 | C16:0 | C18:0 | C18:1 | C18:2 |
|---|---|---|---|---|---|---|---|
| 1.0-6.4 | 2.0-5.0 | 40.0-55.0 | 14.0-18.0 | 6.0-12.0 | 1.0-4.0 | 10.0-21.0 | 1.0-4.0 |

The term "mixture of acyl radicals of a palm kernel oil" thus includes, in this connection, also mixtures of acyl radicals which were originally produced not from palm kernel oil but were adjusted, for example by mixing of synthetic compounds, to the abovementioned acyl radical distribution.

The respective acyl radical content can be determined experimentally by means of a combination of two liquid chromatography methods. In this connection, the individual betaines of the mixture, which comprise from 8 to 18 carbon atoms in the acyl radical, are separated first by means of HPLC/RI according to a method described by R. Gerhards, et al. (Modern methods for the analysis of cocamidopropyl betaines; Gerhards, R., et al.; Tenside, Surfactants, Detergents, 33(1):1-12 (1996)). Since this method gives an insufficient peak separation for the betaines with 16 to 18 carbon atoms (C16, C18:0, C18:1 and C18:2) in the acyl radical, if oleylamidopropyl components are present, this component is separated by means of a second gradient HPLC method. This is carried out on an RP column (reversed phase column, Hypersil Gold 100 mm*3 mm; 5 µm, Thermofisher) at 50° C. in a gradient of 0.05% aqueous ammonium formate solution (pH adjusted to 4.2 with formic acid) and acetonitrile (gradient programme: start with 10% acetonitrile maintained for 1 minute; then a 15 minute linear gradient from 10% to 95% acetonitrile; then maintained for 10 minutes at 95% acetonitrile), the individual betaine fractions being detected by CAD (CAD=charged aerosol detector, Dionex Corona Ultra RS, Thermo Scientific).

The acyl radical contents of the individual betaines, the acyl radicals of which comprise from 8 to 14 carbon atoms, and also the sum of the acyl radical contents of the betaines, the acyl radicals of which comprise from 16 to 18 (C16, C18:0, C18:1 and C18:2) carbon atoms, can consequently be determined from the peak area percentages of the HPLC/RI measurement.

The acyl radical contents of the individual betaines, the acyl radicals of which comprise from 16 to 18 (C16, C18:0, C18:1 and C18:2) carbon atoms, then result from the peak area percentages thereof from the HPLC/CAD measurement after standardizing to the sum of the peak area percentages of these four betaines from the HPLC/RI measurement. For this, the peak area percentage value of the respective betaine from the HPLC/CAD measurement is multiplied by the sum of the peak area percentages of these four betaines from the HPLC/RI measurement and then divided by the sum of the peak area percentages of these four betaines from the HPLC/CAD measurement.

The term "acyl radical content" is always defined as the proportion by weight, based on all acyl radicals present.

The terms "coconut fat" and "coconut oil" are used synonymously.

The terms "palm kernel fat" and "palm kernel oil" are used synonymously.

Unless otherwise stated, all percentages (%) given are percentages by weight.

In an alternative preferred embodiment, the fatty acid amidoalkyl betaines according to the invention are characterized in that the acyl radicals of the mixture exhibit a content of oleic acid acyl radicals, based on all acyl radicals of the mixture, of 19% by weight to 21% by weight.

Preferred fatty acid amidoalkyl betaines according to the invention are characterized in that the mixture of acyl radicals of the palm kernel oil exhibits a linoleic acid acyl radicals (C18:2) content, based on all acyl radicals of the mixture, of 1.5% by weight to 4% by weight, preferably of 2% by weight to 3.5% by weight and particularly preferably of 2.5% by weight to 3% by weight.

Particularly preferred fatty acid amidoalkyl betaines according to the invention are characterized in that the mixture of acyl radicals of the palm kernel oil exhibits a content of oleic acid acyl radicals, based on all acyl radicals of the mixture, of 12% by weight to 21% by weight and a content of linoleic acid acyl radicals, based on all acyl radicals of the mixture, of 2% by weight to 4% by weight, especially a content of oleic acid acyl radicals, based on all acyl radicals of the mixture, of 13% by weight to 21% by weight and a content of linoleic acid acyl radicals, based on all acyl radicals of the mixture, of 2% by weight to 4% by weight.

It is preferred, according to the invention, for the fatty acid amidoalkyl betaines of the present invention to be present in an aqueous solution. The present invention accordingly relates to an aqueous solution comprising the fatty acid amidoalkyl betaines according to the invention. Particularly preferably, the fatty acid amidoalkyl betaines are completely and clearly dissolved in the aqueous solution.

The term "aqueous solution" is understood to mean, in connection with the present invention, compositions with a water content of at least 10% by weight, based on the total composition. The aqueous solution is, according to the invention, preferably liquid at 25° C. and 1 bar pressure. It particularly preferably exhibits, at 25° C., a viscosity in a range from 1 to 9999 mPa·s, the viscosity being determined with a rheometer of Anton Paar, Model MCR 301, plate—plate (40 mm) geometry at a temperature of 25° C. in the shear rate range from $0.1\ s^{-1}$ to $1000\ s^{-1}$.

The aqueous solution according to the invention comprises the fatty acid amidoalkyl betaines according to the invention preferably, based on the total aqueous solution, in an amount of 15% by weight to 55% by weight, preferably of 21% by weight to 49% by weight and particularly preferably of 31% by weight to 39% by weight.

Through this, certain concentrated dishwasher formulations, for example, can be prepared only using comparatively highly concentrated betaines since otherwise the water content of the dishwasher formulation is too high and the proportion of active substances is too low.

The betaine content is calculated either as difference between 100% and the sum of the percentage contents of water, salt and glycerol or, alternatively, as the difference between the percentage dry residue content and the sum of the percentage contents of salt and glycerol. The determinations of content are carried out by a person skilled in the art, for example following Oil and Soap, 22, 115 (1945), and J.A.O.A.C., 26, 99 (1943), and Proc. Sci. Sect. Toilet Goods Ass'n, 5 (1946), and also DIN 51777 and DGF E-III 10 and DGF C-III 13a, and also DGF H-III 9, and also DGF B-II 3/C-III 12.

The aqueous solution comprising the fatty acid amidoalkyl betaines according to the invention preferably exhibits, according to the invention, a pH in a range from 3.1 to 12.9, preferably 3.6 to 7.9 and particularly preferably 4.1 to 6.9.

The "pH" in connection with the present invention is defined as the value which is measured at 25° C. after stirring for 5 minutes using a calibrated pH electrode in accordance with ISO 4319 (1977).

Particularly preferred according to the invention are aqueous solutions comprising fatty acid amidoalkyl betaines according to the invention with n=3 in a concentration, based on the total solution, of 15% by weight to 55% by weight, preferably 21% by weight to 49% by weight and particularly preferably 31% by weight to 39% by weight, characterized in that the mixture of acyl radicals of the palm kernel oil exhibits a content of oleic acid acyl radicals, based on all acyl radicals of the mixture, of 12% by weight to 21% by weight, preferably of 13% by weight to 17% by weight and particularly preferably of 14% by weight to 15% by weight, and particularly preferably the mixture of acyl radicals of the palm kernel oil exhibits a content of linoleic acid acyl radicals, based on all acyl radicals of the mixture, of 2% by weight to 4% by weight.

Very particularly preferred according to the invention are aqueous solutions comprising fatty acid amidoalkyl betaines according to the invention with n=3 in a concentration, based on the total solution, of 15% by weight to 55% by weight, particularly preferably 31% by weight to 39% by weight, characterized in that the mixture of acyl radicals of the palm kernel oil exhibits a content of oleic acid acyl radicals, based on all acyl radicals of the mixture, of 13% by weight to 21% by weight, and particularly preferably the mixture of acyl radicals of the palm kernel oil exhibits a content of linoleic acid acyl radicals, based on all acyl radicals of the mixture, of 2% by weight to 4% by weight.

The fatty acid amidoalkyl betaines according to the invention can be prepared according to processes as described, for example, in DE2926479 or DE4207386 C1.

In order for the fatty acid amidoalkyl betaine content in an aqueous solution to be appropriately increased, water can be removed, for example by evaporation. As a result of the preparation, both the amidamines and the betaines can comprise a low residual content of free fatty acids. This can be determined in the amidamines as acid number and in the betaines as free fatty acid, for example by means of HPLC analysis according to M. J. Cooper and M. W. Anders, *Anal. Chem.*, (12), 1849-1852 (1974). Preferably, according to the invention, the aqueous solution comprises free fatty acids, in particular fatty acids of palm kernel oil. The free fatty acids are, based on the total solution, preferably included in an amount of 0.05% by weight to 2% by weight and particularly preferably of 0.1% by weight to 1.5% by weight.

In addition, it can be advantageous and is accordingly preferred for the solutions according to the invention to comprise glycerol, in particular in an amount of 0.05% by weight to 5% by weight, particularly preferably of 1.0% by weight to 3.0% by weight.

The fatty acid amidoalkyl betaines according to the invention can advantageously be used for the preparation of aqueous formulations, preferably care and cleaning formulations, in particular cosmetic and dermatological formulations. Accordingly, formulations, in particular cosmetic and dermatological formulations, comprising the fatty acid amidoalkyl betaines according to the invention are likewise a subject-matter of the present invention.

Preferred formulations according to the invention additionally include at least one additional surfactant, in particular sodium laureth sulphate. Such formulations are, for example, shampoos, shower gels, bath oils, liquid soaps, mouth rinses, household cleaners, industrial cleaners, dishwasher formulations, textile care compositions and textile finishing compositions.

The present invention is described in exemplary fashion in the examples cited below, without the invention, the scope of application of which results from the whole of the description and the claims, being limited to the embodiments mentioned in the examples.

EXAMPLES

Example 1: Amidamines

As precursors of the betaines, the amidamines were prepared first by reaction, in a known way according to EP 656 346, of dimethylaminopropylamine with the corresponding triglycerides based on fatty acids. Hardened and non-hardened coconut fat and also non-hardened palm kernel fat and mixtures of the abovementioned starting materials were used as triglycerides. When the synthesis was over, all amidamines exhibited an acid number and ester number of at most 2 mg KOH/g:

Amidamine A was prepared from a triglyceride with the following fatty acid chain distribution:

| C8 | 6.6% |
|---|---|
| C10 | 5.6% |
| C12 | 46.4% |
| C14 | 18.7% |
| C16 | 9.9% |
| C18:0 | 11.8% |
| C18:1 | 0.2% |
| others | 0.8% |

Amidamine B was prepared from a triglyceride with the following fatty acid chain distribution:

| C8 | 7.5% |
|---|---|
| C10 | 6.1% |
| C12 | 47.5% |
| C14 | 18.8% |
| C16 | 9.2% |
| C18:0 | 2.8% |
| C18:1 | 6.1% |
| C18:2 | 1.5% |
| others | 0.5% |

Amidamine C was prepared from a triglyceride with the following fatty acid chain distribution:

| C8 | 5.6% |
|---|---|
| C10 | 4.9% |
| C12 | 47.0% |
| C14 | 17.1% |
| C16 | 9.6% |
| C18:0 | 2.6% |
| C18:1 | 11.0% |
| C18:2 | 2.1% |
| others | 0.1% |

Amidamine D was prepared from a triglyceride with the following fatty acid chain distribution:

| C8 | 4.3% |
|---|---|
| C10 | 3.9% |
| C12 | 48.1% |
| C14 | 16.7% |
| C16 | 8.6% |
| C18:0 | 2.5% |
| C18:1 | 13.5% |
| C18:2 | 2.3% |
| others | 0.1% |

Amidamine E was prepared from a triglyceride with the following fatty acid chain distribution:

| C8 | 3.4% |
|---|---|
| C10 | 3.3% |
| C12 | 47.3% |
| C14 | 16.2% |
| C16 | 9.1% |
| C18:0 | 2.2% |
| C18:1 | 15.8% |
| C18:2 | 2.6% |
| others | 0.1% |

Amidamine F was prepared from a triglyceride with the following fatty acid chain distribution:

| C8 | 1.4% |
|---|---|
| C10 | 2.5% |
| C12 | 43.0% |
| C14 | 15.9% |
| C16 | 10.9% |
| C18:0 | 2.8% |
| C18:1 | 19.8% |
| C18:2 | 3.2% |
| others | 0.5% |

Example 2: Betaines (Not According to the Invention)

Synthesis of Betaine A Comprising 0.2% of Oleic Acid Radicals, Based on all Acyl Radicals:

Amidamine A was reacted with sodium monochloroacetate according to EP 0 560 114 to give Betaine A, until the amidamine content fell below 0.5%. The product exhibited a dry residue of 45.8%, an NaCl content of 6.4% and a glycerol content of 2.6%, through which a betaine content of 36.8% was calculated.

Synthesis of Betaine B Comprising 6.0% of Oleic Acid Radicals, Based on all Acyl Radicals:

Amidamine B was reacted with sodium monochloroacetate according to EP 0 560 114 to give Betaine B, until the amidamine content fell below 0.5%. The product exhibited a dry residue of 45.8%, an NaCl content of 6.8% and a glycerol content of 2.6%, through which a betaine content of 36.4% was calculated.

Synthesis of Betaine C Comprising 11.0% of Oleic Acid Radicals, Based on all Acyl Radicals:

Amidamine C was reacted with sodium monochloroacetate according to EP 0 560 114 to give Betaine C, until the amidamine content fell below 0.5%. The product exhibited a dry residue of 45.5%, an NaCl content of 7.4% and a glycerol content of 2.5%, through which a betaine content of 35.6% was calculated.

Example 3: Betaines (According to the Invention)

Synthesis of Betaine D Comprising 13.5% of Oleic Acid Radicals, Based on all Acyl Radicals:

On the basis of the comparatively high proportion of C18 and of a strong increase in viscosity resulting therefrom in a known way during the synthesis in approximately 45% aqueous solution, Amidamine D was first reacted with sodium monochloroacetate to give a Betaine D* with a dry residue of 37%, until the amidamine content fell below 0.4%. Subsequently, Betaine D was prepared by evaporating so much water that a solution with a dry weight content of 45.1%, an NaCl content of 7.8% and a glycerol content of 2.4% was obtained, resulting in a betaine content, based on the entire solution, of 34.9%.

Synthesis of Betaine E Comprising 15.8% of Oleic Acid Radicals, Based on all Acyl Radicals:

On the basis of the comparatively high proportion of C18 and of a strong increase in viscosity resulting therefrom in a known way during the synthesis in approximately 45% aqueous solution, Amidamine E was first reacted with sodium monochloroacetate to give a Betaine E* with a dry residue of 37%, until the amidamine content fell below 0.4%. Subsequently, Betaine E was prepared by evaporating so much water that a solution with a dry weight content of 44.3%, an NaCl content of 7.6% and a glycerol content of 2.3% was obtained, resulting in a betaine content, based on the entire solution, of 34.4%.

Synthesis of Betaine F Comprising 19.8% of Oleic Acid Radicals, Based on all Acyl Radicals:

On the basis of the comparatively high proportion of C18 and of a strong increase in viscosity resulting therefrom in a known way during the synthesis in approximately 45% aqueous solution, Amidamine F was first reacted with sodium monochloroacetate to give a Betaine F* with a dry residue of 37%, until the amidamine content fell below 0.4%. Subsequently, Betaine F was prepared by evaporating so much water that a solution with a dry weight content of 45.0%, an NaCl content of 7.3% and a glycerol content of 2.4% was obtained, resulting in a betaine content, based on the entire solution, of 35.3%.

After the synthesis, it was confirmed, for all Betaines A to F, that their fatty acid chain distribution corresponds to that of the triglycerides used above.

Example 4: Thickenability of Cosmetic Formulations

Thickenability was tested in a very common standard surfactant system. The formulation constituents are named in the compositions in the form of the generally recognized INCI nomenclature using the English terms. All concentrations in the application examples are given in percentage by weight. The viscosity determination was carried out using a Brookfield viscometer (Brookfield LVF, spindle 2, 30 rpm) at 25° C.

The data in Tables 3 and 4 verify that formulations which differ exclusively in the betaine used exhibit a clearly higher viscosity if, instead of Betaine A or B not according to the invention, Betaine E or F according to the invention is used.

The data in Table 5 show that a specified formulation viscosity is already achieved through addition of smaller amounts of the betaines according to the invention than through addition of betaines not according to the invention.

TABLE 3

Viscosity comparison in a standard surfactant formulation

| | | | | |
|---|---|---|---|---|
| Texapon ® NSO, BASF SE, 28% (INCI: Sodium Laureth Sulfate) | 32.0% | 32.0% | 32.0% | 32.0% |
| Betaine A | 8.0% | | | |
| Betaine B | | 8.0% | | |
| Betaine E | | | 8.0% | |
| Betaine F | | | | 8.0% |
| Antil ® 171, Evonik Industries AG (INCI: PEG-18 Glyceryl Cocoate/Oleate) | 2.5% | 2.5% | 2.5% | 2.5% |
| Sodium chloride | 0.5% | 0.5% | 0.5% | 0.5% |
| Water | to 100% | to 100% | to 100% | to 100% |
| Citric Acid, 30% | to pH 5.5 | to pH 5.5 | to pH 5.5 | to pH 5.5 |
| Viscosity [mPa · s] | 3115 | 4395 | 6677 | 8152 |

TABLE 4

Viscosity comparison depending on the salt concentration in an aqueous formulation of 32% Texapon ® NSO (BASF SE, 28%) and 8% Betaine

| | Salt content of the formulation | | | |
|---|---|---|---|---|
| | 1% NaCl | 2% NaCl | 3% NaCl | 4% NaCl |
| Viscosity [mPa · s] with Betaine A | 32 | 5226 | 6528 | 24930 |
| Viscosity [mPa · s] with Betaine E | 533 | 6218 | 45820 | 96530 |

TABLE 5

Betaine contents required for a formulation viscosity of 3500 mPa · s

| | | | | |
|---|---|---|---|---|
| Texapon ® NSO, BASF SE, 28% (INCI: Sodium Laureth Sulfate) | 32.0% | 32.0% | | |
| Betaine A | 8.0% | | 12.8% | |
| Betaine E | | 6.9% | | 6.7% |
| Rewoteric ® AM C, Evonik Industries AG (INCI: Sodium Cocoamphoacetate) | | | 15.0% | 15.0% |
| Rewopol ® SB F 12 P, Evonik Industries AG (INCI: Disodium Lauryl Sulfosuccinate) | | | 3.6% | 3.6% |
| Antil ® 171, Evonik Industries AG (INCI: PEG-18 Glyceryl Cocoate/Oleate) | 2.5% | 2.5% | 3.8% | 3.8% |
| Sodium chloride | 0.5% | 0.5% | | |
| Water | to 100% | to 100% | to 100% | to 100% |
| Citric Acid, 30% | to pH 5.5 | to pH 5.5 | to pH 5.5 | to pH 5.5 |
| Viscosity [mPa · s] | 3500 | 3500 | 3500 | 3500 |

Example 5: Foaming Behaviour

In SITA measurements (c=0.5%, T=30° C., water with 10° dH (German hardness), pH=6, 1500 rpm), Betaines D and E according to the invention showed, in comparison with Betaines A and C not in accordance with the invention, a clearly better foaming behaviour. The results are shown in Table 6.

TABLE 6

Foaming behaviour in 0.5% aqueous solution

| | Stirring time [s] | | | | | |
|---|---|---|---|---|---|---|
| | 10 | 20 | 30 | 40 | 50 | 60 |
| Foam height Betaine A [mm] | 330 | 507 | 763 | 973 | 1022 | 1044 |
| Foam height Betaine C [mm] | 356 | 530 | 807 | 976 | 1042 | 1061 |
| Foam height Betaine D [mm] | 494 | 771 | 941 | 1019 | 1051 | 1067 |
| Foam height Betaine E [mm] | 591 | 1031 | 1031 | 1039 | 1047 | 1054 |

Example 6: Softness and Stiffness After Betaine Application on Woven Fabric

In order to compare softness and stiffness, the betaines were applied using a padding machine to knitted fabrics of wfk-Testgewebe GmbH (roller application, type HVF, Mathis AG, application from a 0.25% (active) bath=0.003 g/g for the softness measurements, drying of the fabric in a laboratory dryer (type LTE, Mathis AG) at 105° C. for 2 minutes plus residence time and fixing at 150° C. for 3 minutes without residence time, storage of the textiles for approximately 24 hours in a climatic chamber at 23° C. and 50% atmospheric humidity) and then measurements using a Tissue Softness Analyzer from Emtec Electronic GmbH were carried out. The results are shown in Table 7 as average values of 5 individual measurements. In the case of the softness parameter, the application of Betaine D according to the invention proved to be advantageous in comparison with Betaines A and C not according to the invention, since lower values mean an enhanced softness. In the case of the stiffness parameter, higher values indicated a reduced stiffness, the application of Betaine D according to the invention here also proving to be advantageous in comparison with Betaines A and C not according to the invention.

TABLE 7

| TSA measurement results | | |
|---|---|---|
| | Softness | Stiffness [mm/N] |
| Betaine A [mm] | 11.4 | 2.75 |
| Betaine C [mm] | 11.4 | 2.78 |
| Betaine D [mm] | 10.7 | 2.93 |

Example 7: Preparation of Highly Concentrated Dishwasher Formulations

As emerges from Table 8, the preparation of a highly concentrated dishwasher formulation following DE102007005942 was successful only with the use of the comparatively highly concentrated Betaine D, in contrast to the Betaine D* having a lower concentration, if, as in the present example, processing is carried out with a 28% aqueous sodium lauryl ether sulphate solution, which, on the basis of the low viscosity and cold processability, represents the market standard.

TABLE 8

| Preparation of highly concentrated dishwater formulations with a pH of 6 | | | | |
|---|---|---|---|---|
| Raw material | Raw material concentration | Active substance/ betaine content desired in formulation | Raw material amount | Raw material amount |
| Texapon ® NSO | 28.0% | 21.0% | 75.0% | 75.0% |
| Betaine D* | 37.0% (28.6% betaine) | 7.0% | 24.5% | |
| Betaine D | 45.1% (34.9% betaine) | 7.0% | | 20.0% |
| Ethanol | 99.8% | 5.0% | 5.0% | 5.0% |
| Sum | | | 104.5% | 100% |

All references cited herein are fully incorporated by reference in their entirety. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. An aqueous solution comprising a fatty acid amidoalkyl betaine of formula I:

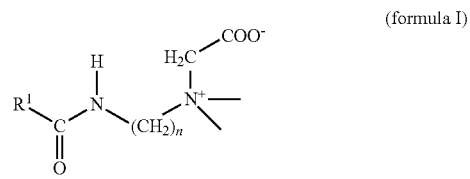

(formula I)

wherein:
n=1 to 10, and
$R^1CO$=mixture of acyl radicals of a palm kernel oil,
wherein the mixture of the acyl radicals exhibits an oleic acid acyl radicals content, based on all acyl radicals of the mixture, of 13% by weight to 17% by weight;
and wherein the aqueous solution comprises fatty acid amidoalkyl betaines in an amount of 15% by weight to 55% by weight.

2. The aqueous solution of claim 1, wherein, in formula I, n=2 to 5.

3. The aqueous solution of claim 1, wherein, in formula I, n=3.

4. The aqueous solution of claim 1, wherein the mixture of acyl radicals exhibits an oleic acid acyl radicals content, based on all acyl radicals of the mixture, of 14% by weight to 15% by weight.

5. The aqueous solution of claim 1, wherein, in formula I, n=3 and the mixture of the acyl radicals exhibits an oleic acid acyl radicals content, based on all acyl radicals of the mixture, of 14% by weight to 15% by weight.

6. The aqueous solution of claim 1, wherein, the mixture of acyl radicals of the palm kernel oil exhibits a linoleic acid acyl radicals (C18:2) content, based on all acyl radicals of the mixture, of 1.5% by weight to 4% by weight.

7. The aqueous solution of claim 1, wherein the mixture of acyl radicals of the palm kernel oil exhibits a linoleic acid acyl radicals (C18:2) content, based on all acyl radicals of the mixture, of 2% by weight to 3.5% by weight.

8. The aqueous solution of claim 1, wherein the mixture of acyl radicals of the palm kernel oil exhibits a linoleic acid acyl radicals (C18:2) content, based on all acyl radicals of the mixture, of 2.5% by weight to 3% by weight.

9. The aqueous solution of claim 1, wherein the mixture of acyl radicals of the palm kernel oil exhibits a content of linoleic acid acyl radicals, based on all acyl radicals of the mixture, of 2% by weight to 4% by weight.

10. The aqueous solution of claim 1, wherein said aqueous solution comprises fatty acid amidoalkyl betaines in an amount of 21% by weight to 49% by weight.

11. The aqueous solution of claim 1, wherein said aqueous solution comprises fatty acid amidoalkyl betaines in an amount of 31% by weight to 39% by weight.

12. The aqueous solution of claim 1, wherein said aqueous solution exhibits a pH in a range from 3.6 to 7.9.

13. The aqueous solution of claim 1, wherein said aqueous solution exhibits a pH in a range from 4.1 to 6.9.

14. The aqueous solution of claim 1, wherein said aqueous solution comprises free fatty acids.

15. The aqueous solution of claim 1, wherein said aqueous solution comprises glycerol.

16. The aqueous solution of claim 1, wherein said aqueous solution comprises an additional surfactant.

17. An aqueous solution comprising a fatty acid amidoalkyl betaine of formula I:

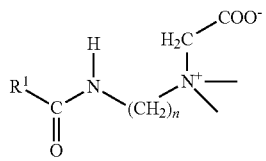

(formula I)

wherein:
n=1 to 10, and
$R^1CO$=mixture of acyl radicals of a palm kernel oil,
wherein the mixture of the acyl radicals exhibits an oleic acid acyl radicals content, based on all acyl radicals of the mixture, of 13% by weight to 17% by weight;
and wherein, compared to an aqueous solution in which the mixture of the acyl radicals exhibits an oleic acid acyl radicals content, based on all acyl radicals of the mixture, of 11% by weight or lower, said aqueous solution exhibits faster foam development.

18. The aqueous solution of claim 17, wherein, in formula I, n=2 to 5.

19. The aqueous solution of claim 18, wherein, the mixture of acyl radicals of the palm kernel oil exhibits a linoleic acid acyl radicals (C18:2) content, based on all acyl radicals of the mixture, of 1.5% by weight to 4% by weight.

20. The aqueous solution of claim 19, wherein said aqueous solution comprises fatty acid amidoalkyl betaines in an amount of 21% by weight to 49% by weight.

* * * * *